United States Patent [19]
Young

[11] 3,962,364
[45] June 8, 1976

[54] ALKYLATION IN PRESENCE OF PHOSPHORUS-MODIFIED CRYSTALLINE LUMINOSILICATE CATALYST

[75] Inventor: Lewis Brewster Young, Kendall Park, N.J.

[73] Assignee: Mobil Oil Corporation, New York, N.Y.

[22] Filed: Mar. 28, 1975

[21] Appl. No.: 563,286

[52] U.S. Cl. .......................... 260/671 C; 252/437; 260/671 R
[51] Int. Cl.[2] .......................................... C07C 3/52
[58] Field of Search ................... 260/671 R, 671 C; 252/435, 437, 464

[56] References Cited
UNITED STATES PATENTS

| | | | |
|---|---|---|---|
| 3,725,243 | 4/1973 | Hess et al. ........................... | 252/435 |
| 3,791,964 | 2/1974 | Kuehl ................................. | 252/435 |
| 3,867,305 | 2/1975 | Flanigen et al. .................... | 252/437 |
| 3,899,544 | 8/1975 | Chang et al. ....................... | 260/668 C |
| 3,906,054 | 9/1975 | Kaeding et al. ..................... | 260/682 |
| 3,911,041 | 10/1975 | Kaeding et al. ................... | 260/668 R |

*Primary Examiner*—C. Davis
*Attorney, Agent, or Firm*—Charles A. Huggett; Raymond W. Barclay

[57] ABSTRACT

Process for the alkylation of aromatic hydrocarbons by contacting same with an olefin alkylating agent in a reaction zone maintained under conditions such that said alkylation is accomplished in the vapor phase and in the presence of a catalyst comprising a crystalline aluminosilicate zeolite, said zeolite having a silica to alumina ratio of at least about 12 and a constraint index, as hereinafter defined, of from 1 to 12, said catalyst having been modified by the addition thereto of phosphorus in an amount of at least about 0.5 percent by weight.

20 Claims, 1 Drawing Figure

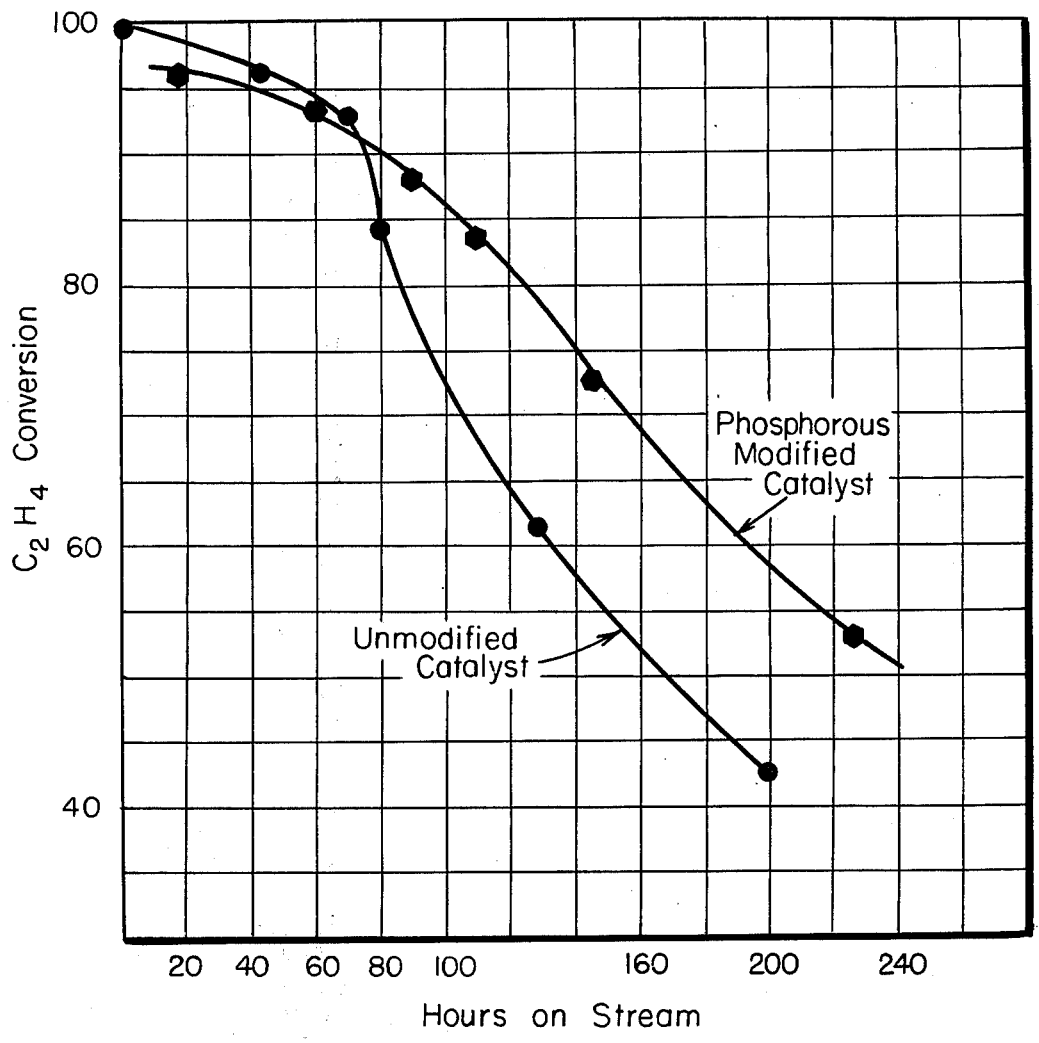

ALKYLATION IN PRESENCE OF PHOSPHORUS-MODIFIED CRYSTALLINE LUMINOSILICATE CATALYST

BACKGROUND OF THE INVENTION

1. Field of the Invention

This invention relates to a process for the alkylation of an aromatic hydrocarbon by reaction with an olefin in the presence of a crystalline aluminosilicate catalyst modified by the addition thereto of phosphorus.

2. Description of the Prior Art

Alkylation of aromatic hydrocarbons utilizing crystalline aluminosilicate catalysts has heretofore been described. U.S. Pat. No. 2,904,607 to Mattox refers to alkylation of aromatic hydrocarbons with an olefin in the presence of a crystalline metallic aluminosilicate having uniform pore openings of about 6 to 15 Angstrom units. U.S. Pat. No. 3,251,897 to Wise describes liquid phase alkylation in the presence of X- or Y-type crystalline aluminosilicate zeolites, specifically such type zeolites wherein the cation is rare earth and/or hydrogen. U.S. Pat. No. 3,751,504 to Keown et al, and U.S. Pat. No. 3,751,506 to Burress describe vapor phase alkylation of aromatic hydrocarbons with olefins, e.g. benzene with ethylene, in the presence of a ZSM-5 type zeolite catalyst.

While the latter type catalysts represent a distinct improvement over previously suggested crystalline aluminosilicate catalysts particularly with respect to improved aging properties, they have the disadvantage of producing unwanted quantities of impurities along with the desired alkyl aromatic product, thereby decreasing the overall yield and selectivity for such product.

SUMMARY OF THE INVENTION

In accordance with the present invention, there has been discovered a process for improving the selectivity for the desired alkyl aromatic product, i.e. decreasing the formation of unwanted impurities while simultaneously improving the aging characteristics of the catalyst to afford a high yield of the alkylate of interest over a long commercially attractive period of time.

The process comprises effecting vapor phase alkylation of aromatic hydrocarbons by contacting the same with an olefin under conditions effective for accomplishing said vapor phase alkylation including a reactor inlet temperature between about 575°F. and 900°F., with a reactor bed temperature as much as 250°F. above the reactor inlet temperature, a pressure between atmospheric and 3000 p.s.i.g., employing a mole ratio of aromatic hydrocarbon to olefin alkylating agent in the approximate range of 1:1 to 30:1 and a total feed weight hourly space velocity between about 2 and about 2000, in the presence of a catalyst comprising a crystalline aluminosilicate zeolite, said zeolite having a silica to alumina ratio of at least about 12, a constraint index of from 1 to 12 and which has been modified by the addition thereto of phosphorus in an amount of at least about 0.5 percent by weight. The content of phosphorus may be as high as about 25 percent by weight.

BRIEF DESCRIPTION OF THE DRAWING

The single FIGURE of the drawing depicts the effect of aging on ethylene conversion for the phosphorus-modified catalyst described herein as compared with the unmodified catalyst.

DESCRIPTION OF SPECIFIC EMBODIMENTS

The zeolite catalysts herein described are members of a novel class of zeolites exhibiting some unusual properties. These catalysts induce profound transformations of aliphatic hydrocarbons to aromatic hydrocarbons in commercially desirable yields and are generally highly effective in conversion reactions involving aromatic hydrocarbons. Although they have unusually low alumina contents, i.e. high silica to alumina ratios, they are very active even when the silica to alumina ratio exceeds 30. The activity is surprising since catalytic activity is generally attributed to framework aluminum atoms and cations associated with these aluminum atoms. These catalysts retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type catalysts useful in this invention possess, in combination: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although catalysts with a silica to alumina ratio of at least 12 are useful, it is preferred to use catalysts having higher ratios of at least about 30. Such catalyst, after activation, acquire an intracrystalline sorption capacity for normal hexane which is greater than that for water, i.e. they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these catalysts ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather then attempt to judge from crystal structure whether or not a catalyst possesses the necessary constrained access, a simple determination of the "constraint index" may be made by passing continuously a mixture of an equal weight of normal hexane and 3-methylpentane over a small sample, approximately 1 gram or less, of catalyst at atmospheric pressure according to the following procedure. A sample of the catalyst, in the form of pellets or extrudate, is crushed to a particle size about that of coarse sand and mounted in a glass tube. Prior to testing, the catalyst is treated with a stream of air at 1000°F. for at least 15 minutes. The catalyst is then flushed with helium and the temperature adjusted between 550°F. and 950°F. to give an overall conversion between 10% and 60%. The mixture of hydrocarbons is passed at 1 liquid hourly space velocity (i.e., 1 volume of liquid hydrocarbon per volume of catalyst per hour) over the catalyst with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10} (\text{fraction of n-hexane remaining})}{\log_{10} (\text{fraction of 3-methylpentane remaining})}$$

The constraint index approximates the ratio of the cracking rate constants for the two hydrocarbons. Catalysts suitable for the present invention are those having a constraint index in the approximate range of 1 to 12. Constraint Index (CI) values for some typical catalysts are:

| CAS | C.I. |
|---|---|
| ZSM-5 | 8.3 |
| ZSM-11 | 8.7 |
| ZSM-12 | 2 |
| ZSM-38 | 2 |
| ZSM-35 | 4.5 |
| TMA Offretite | 3.7 |
| Beta | 0.6 |
| ZSM-4 | 0.5 |
| H-Zeolon | 0.5 |
| REY | 0.4 |
| Amorphous Silica-Alumina | 0.6 |
| Erionite | 38 |

It is to be realized that above constraint index values typically characterize the specified zeolites but that such are the cumulative result of several variables used in determination and calculation thereof. Thus, for a given zeolite depending on the temperature employed within the aforenoted range of 550°F. to 950°F., with accompanying conversion between 10% and 60%, the constraint index may vary within the indicated approximate range of 1 to 12. Likewise, other variables such as the crystal size of the zeolite, the presence of possibly occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with the probability, in some instances, of compounding variable extremes. However, in all instances, at a temperature within the above-specified range of 550°F. to 950°F., the constraint index will have a value for any given zeolite of interest herein within the approximate range of 1 to 12.

The class of zeolites defined herein is exemplified by ZSM-5, ZSM-11, ZSM-12, ZSM-35, ZSM-38, and other similar materials. Recently issued U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-38 is more particularly described in U.S. application Ser. No. 528,060, filed Nov. 29, 1974. This zeolite can be identified, in terms of mole ratios of oxides and in the anhydrous state, as follows:

$$(0.3-2.5)R_2O : (0-0.8)M_2O : Al_2O_3 : > 8\ SiO_2$$

wherein R is an organic nitrogen-containing cation derived from a 2-(hydroxyalkyl) trialkylammonium compound and M is an alkali metal cation, and is characterized by a specified X-ray powder diffraction pattern.

In a preferred synthesized form, the zeolite has a formula, in terms of mole ratios of oxides and in the anhydrous state, as follows:

$$(0.4-2.5)R_2O : (0-0.6)\ M_2O : Al_2O_3 : xSiO_2$$

wherein R is an organic nitrogen-containing cation derived from a 2-(hydroxyalkyl) trialkylammonium compound, wherein alkyl is a methyl, ethyl or a combination thereof, M is an alkali metal, especially sodium, and $x$ is from greater than 8 to about 50.

The synthetic ZSM-38 zeolite possesses a definite distinguishing crystalline structure whose X-ray diffraction pattern shows substantially the significant lines set forth in Table I. It is observed that this X-ray diffraction pattern (significant lines) is similar to that of natural ferrierite with a notable exception being that natural ferrierite patterns exhibit a significant line at 11.33A.

TABLE I

| d(A) | I/Io |
|---|---|
| 9.8 ± 0.20 | Strong |
| 9.1 ± 0.19 | Medium |
| 8.0 ± 0.16 | Weak |
| 7.1 ± 0.14 | Medium |
| 6.7 ± 0.14 | Medium |
| 6.0 ± 0.12 | Weak |
| 4.37 ± 0.09 | Weak |
| 4.23 ± 0.09 | Weak |
| 4.01 ± 0.08 | Very Strong |
| 3.81 ± 0.08 | Very Strong |
| 3.69 ± 0.07 | Medium |
| 3.57 ± 0.07 | Very Strong |
| 3.51 ± 0.07 | Very Strong |
| 3.34 ± 0.07 | Medium |
| 3.17 ± 0.06 | Strong |
| 3.08 ± 0.06 | Medium |
| 3.00 ± 0.06 | Weak |
| 2.92 ± 0.06 | Medium |
| 2.73 ± 0.06 | Weak |

TABLE I-continued

| d(A) | I/Io |
|---|---|
| 2.66 ± 0.05 | Weak |
| 2.60 ± 0.05 | Weak |
| 2.49 ± 0.05 | Weak |

A further characteristic of ZSM-38 is its sorptive capacity providing said zeolite to have increased capacity for 2-methylpentane (with respect to n-hexane sorption by the ratio n-hexane/2-methyl-pentane) when compared with a hydrogen form of natural ferrierite resulting from calcination of an ammonium exchanged form. The characteristic sorption ratio n-hexane/2-methylpentane for ZSM-38 (after calcination at 600°C.) is less than 10, whereas that ratio for the natural ferrierite is substantially greater than 10, for example, as high as 34 or higher.

Zeolite ZSM-38 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| R+ + M+ | 0.2–1.0 | 0.3–0.9 |
| OH$^-$/SiO$_2$ | 0.05–0.5 | 0.07–0.49 |
| H$_2$O/OH$^-$ | 41–500 | 100–250 |
| SiO$_2$/Al$_2$O$_3$ | 8.8–200 | 12–60 | wherein R is an organic nitrogen-containing cation derived from a 2-(hydroxyalkyl) trialkylammonium compound and M is an alkali metal ion, and maintaining the mixture until crystals of the zeolite are formed. (The quantity of OH$^-$ is calculated only from the inorganic sources of alkali without any organic base contribution). Thereafter, the crystals are separated from the liquid and recovered. Typical reaction conditions consist of heating the foregoing reaction mixture to a temperature of from about 90°C. to about 400°C. for a period of time of from about 6 hours to about 100 days. A more preferred temperature range is from about 150°C. to about 400°C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is thereafter dried, e.g. at 230°F. for from about 8 to 24 hours.

ZSM-35 is more particularly described in U.S. application Ser. No. 528,061, filed Nov. 29, 1974. This zeolite can be identified, in terms of mole ratios of oxides and in the anhydrous state, as follows:

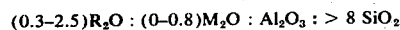

(0.3–2.5)R$_2$O : (0–0.8)M$_2$O : Al$_2$O$_3$ : > 8 SiO$_2$ wherein R is an organic nitrogen-containing cation derived from ethylenediamine or pyrrolidine and M is an alkali metal cation, and is characterized by a specified X-ray powder diffraction pattern.

In a preferred synthesized form, the zeolite has a formula, in terms of mole ratios of oxides and in the anhydrous state, as follows:

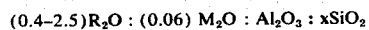

(0.4–2.5)R$_2$O : (0.06) M$_2$O : Al$_2$O$_3$ : xSiO$_2$ wherein R is an organic nitrogen-containing cation derived from ethylenediamine or pyrrolidine, M is an alkali metal, especially sodium, and x is from greater than 8 to about 50.

The synthetic ZSM-35 zeolite possesses a definite distinguishing crystalline structure whose X-ray diffraction pattern shows substantially the significant lines set forth in Table II. It is observed that this X-ray diffraction pattern (with respect to significant lines) is similar to that of natural ferrierite with a notable exception being that natural ferrierite patterns exhibit a significant line at 11.33A. Close examination of some individual samples of ZSM-35 may show a very weak line at 11.3–11.5A. This very weak line, however, is determined not to be a significant line for ZSM-35.

TABLE II

| d(A) | I/Io |
|---|---|
| 9.6 ± 0.20 | Very Strong – Very Very Strong |
| 7.10 ± 0.15 | Medium |
| 6.98 ± 0.14 | Medium |
| 6.64 ± 0.14 | Medium |
| 5.78 ± 0.12 | Weak |
| 5.68 ± 0.12 | Weak |
| 4.97 ± 0.10 | Weak |
| 4.58 ± 0.09 | Weak |
| 3.99 ± 0.08 | Strong |
| 3.94 ± 0.08 | Medium Strong |
| 3.85 ± 0.08 | Medium |
| 3.78 ± 0.08 | Strong |
| 3.74 ± 0.08 | Weak |
| 3.66 ± 0.07 | Medium |
| 3.54 ± 0.07 | Very Strong |
| 3.48 ± 0.07 | Very Strong |
| 3.39 ± 0.07 | Weak |
| 3.32 ± 0.07 | Weak Medium |
| 3.14 ± 0.06 | Weak Medium |
| 2.90 ± 0.06 | Weak |
| 2.85 ± 0.06 | Weak |
| 2.71 ± 0.05 | Weak |
| 2.65 ± 0.05 | Weak |
| 2.62 ± 0.05 | Weak |
| 2.58 ± 0.05 | Weak |
| 2.54 ± 0.05 | Weak |
| 2.48 ± 0.05 | Weak |

A further characteristic of ZSM-35 is its sorptive capacity proving said zeolite to have increased capacity for 2-methylpentane (with respect to n-hexane sorption by the ratio n-hexane/2-methylpentane) when compared with a hydrogen form of natural ferrierite resulting from calcination of an ammonium exchanged form. The characteristic sorption ratio n-hexane/2-methylpentane for ZSM-35 (after calcination at 600°C.) is less than 10, whereas that ratio for the natural ferrierite is substantially greater than 10, for example, as high as 34 or higher.

Zeolite ZSM-35 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| R+ + M+ | 0.2–1.0 | 0.3–0.9 |
| OH$^-$/SiO$_2$ | 0.05–0.5 | 0.07–0.49 |
| H$_2$O/OH$^-$ | 41–500 | 100–250 |
| SiO$_2$/Al$_2$O$_3$ | 8.8–200 | 12–60 | wherein R is an organic nitrogen-containing cation derived from pyrrolidine or ethylenediamine and M is an alkali metal ion, and maintaining the mixture until crystals of the zeolite are formed. (The quantity of OH⁻ is calculated only from the inorganic sources of alkali without any organic base contribution). Thereafter, the crystals are separated from the liquid and recovered. Typical reaction conditions consist of heating the foregoing reaction mixture to a temperature of from about 90°C. to about 400°C. for a period of time of from about 6 hours to about 100 days. A more preferred temperature range is from about 150°C. to about 400°C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is dried, e.g. at 230°F., for from about 8 to 24 hours.

The specific zeolites described, when prepared in the presence of organic cations, are catalytically inactive, possible because the intracrystalline free space is occupied by organic cations from the forming solution. They may be activated by heating in an inert atmosphere at 1000°F. for 1 hour, for example, followed by base exchange with ammonium salts followed by calcination at 1000°F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000°F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so streated include ferrierite, brewsterite, stilbite, dachiardite, epistilbite, heulandite, and clinoptilolite. The preferred crystalline aluminosilicates are ZSM-5, ZSM-11, ZSM-12, ZSM-38 and ZSM-35, with ZSM-5 particularly preferred.

The catalysts of this invention may be in the hydrogen form or they may be base exchanged or impregnated to contain ammonium or a metal cation complement. It is desirable to calcine the catalyst after base exchange. The metal cations that may be present include any of the cations of the metals of Groups I through VIII of the periodic table. However, in the case of Group IA metals, the cation content should in no case be so large as to effectively inactivate the catalyst.

In a preferred aspect of this invention, the catalysts hereof are selected as those having a crystal framework density, in the dry hydrogen form, of not substantially below about 1.6 grams per cubic centimeter. It has been found that zeolites which satisfy all three of these criteria are most desired because they tend to maximize the production of gasoline boiling range hydrocarbon products. Therefore, the preferred catalysts of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meir. This paper, the entire contents of which are incorporated herein by reference, is included in "Proceedings of the Conference on Molecular Sieves, London, April 1967", published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
| --- | --- | --- |
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table including, by way of example, nickel, zinc, calcium or rare earth metals.

The crystals of zeolite in a form substantially free of alkali metal, i.e. containing less than about 1.5 weight percent alkali metal and preferably having at least a portion of the original cations associated therewith replaced by hydrogen, are then contacted with a phosphorus compound.

Representative phosphorus-containing compounds include derivatives of groups represented by $PX_3$, $RPX_2$, $R_2PX$, $R_3P$, $X_3PO$, $(XO_3)PO$, $(XO)_3P$, $R_3P=O$, $R_3P=S$, $RPO_2$, $PPS_2$, $RP(O)(Ox)_2$, $RP(S)(Sx)_2$, $R_2P(O)(Ox)$, $R_2P(S)Sx$, $RP(OX)_2$, $RP(Sx)_2ROP(Ox)_2$, $RSP(Sx)_2$, $(RS)_2PSP(SR)_2$, and $(RO)_2POP(OR)_2$, where R is an alkyl or aryl, such as a phenyl radical and X is hydrogen, R, or halide. These compounds include primary, $RPH_2$, secondary, $R_2PH$ and tertiary, $R_3P$, phosphines such as butyl phosphine; the tertiary phosphine oxides $R_3PO$, such as tributylphosphine oxide, the tertiary phosphine sulfides, $R_3PS$, the primary, $RP(O)(OX)_2$, and secondary, $R_2P(O)OX$, phosphonic acids such as benzene phosphonic acid; the corresponding sulfur derivatives such as $RP(S)(SX)_2$ and $R_2P(S)SX$, the esters of the phosphonic acids such as diethyl phosphonate, $(RO)_2P(O)H$, dialkyl alkyl phosphonates, $(RO)_2P(O)R$, and alkyl dialkylphosphinates, $(RO)P(O)R_2$; phosphinous acids, $R_2POX$, such as diethylphosphinous acid, primary, $(RO)P(OX)_2$, secondary, $(RO)_2POX$, and tertiary, $(RO)_3P$, phosphites; and esters thereof such as the monopropyl ester, alkyl dialkylphosphinites, $(RO)PR_2$, and dialkyl alkylphosphonite, $(RO)_2PR$ esters. Corresponding sulfur derivatives may also be employed including $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RS)PR_2$ and $(RS)_2PR$. Examples of phosphite esters include trimethylphosphite, triethylphosphite, diisopropylphosphite, butylphosphite; and pyrophosphites such as tetraethylpyrophosphite. The alkyl groups in the mentioned compounds contain 1 to 4 carbon atoms.

Other suitable phosphorus-containing compounds include the phosphorus halides such as phosphorus trichloride, bromide, and iodide, alkyl phosphorodichloridites, $(RO)PCl_2$, dialkyl phosphorochloridites, $(RO)_2PX$, dialkylphosphionochloridites, $R_2PCl$, alkyl alkylphosphonochloridates, $(RO)(R)P(O)Cl$, dialkyl phosphinochloridates, $R_2P(O)Cl$ and $RP(O)Cl_2$. Applicable corresponding sulfur derivatives include $(RS)PCl_2$, $(RS)_2PX$, $(RS)(R)P(S)Cl$ and $R_2P(S)Cl$.

Preferred phosphorus-containing compounds include diphenyl phosphine chloride, trimethylphosphite and phosphorus trichloride, phosphoric acid, phenyl phosphine oxychloride, trimethylphosphate, diphenyl phosphinous acid, diphenyl phosphinic acid, diethylchloro thiophosphate, methyl acid phosphate and other alcohol-$P_2O_5$ reaction products.

Incorporation of phosphorus with the zeolite provides a compoosition having unique properties as a catalytic agent. Thus, the so treated zeolite possesses a greater number of acid sites than the parent zeolite but these sites appear to have a lesser acid strength than those found in the parent zeolite. It is believed that the apparent replacement of the strong acid sites with a greater number of relatively weak acid sites may be responsible for the unique catalytic properties of the phosphorus-containing zeolite.

Reaction of the zeolite with the phosphorus compound is effected by contacting the zeolite with such compound. Where the treating phosphorus compound is a liquid, such compound can be in solution in a solvent at the time contact with the zeolite is effected. Any solvent relatively inert with respect to the treating compound and the zeolite may be employed. Suitable solvents include water and aliphatic, aromatic or alcoholic liquids. Where the phosphorus-containing compound is, for example, trimethylphosphite or liquid phosphorus trichloride, a hydrocarbon solvent such as n-octane may be employed. The phosphorus-containing compound may be used without a solvent, i.e., may be used as a neat liquid. Where the phosphorus-containing compound is in the gaseous phase, such as where gaseous phosphorus trichloride is employed, the treating compound can be used by itself or can be used in admixture with a gaseous diluent relatively inert to the phosphorus-containing compound and the zeolite such as air or nitrogen or with an organic solvent, such as octane or toluene.

Prior to reacting the zeolite with the phosphorus-containing compound, the zeolite may be dried. Drying can be effected in the presence of air. Elevated temperatures may be employed. However, the temperature should not be such that the crystal structure of the zeolite is destroyed.

Heating of the phosphorus-containing catalyst subsequent to preparation and prior to use is also preferred. The heating can be carried out in the presence of oxygen, for example air. Heating can be at a temperature of about 150°C. However, higher temperatures, i.e., up to about 500°C. are preferred. Heating is generally carried out for 3–5 hours but may be extended to 24 hours or longer. While heating temperatures above about 500°C. can be employed, they are not necessary. At temperatures of about 1000°C., the crystal structure of the zeolite tends to deteriorate.

The amount of phosphorus incorporated with the zeolite should be at least about 0.5 percent by weight. With this amount of phosphorus, replacement of a sufficient proportion of the strong acid sites of the zeolite with an increased number of weak acid sites is effected. However, it is preferred in order to increase the replacement of the strong acid sites with an increased number of these weaker acid sites that the amount of phosphorus in the zeolite be at least about 2 percent by weight when the same is combined with a binder, e.g. 35 weight percent of alumina. The amount of phosphorus can be as high as about 25 percent by weight or more depending on the amount and type of binder present. Preferably, the amount of phosphorus added to the zeolite is between about 0.7 and about 15 percent by weight.

The amount of phosphorus incorporated with the zeolite by reaction with elemental phosphorus or phosphorus-containing compound will depend upon several factors. One of these is the reaction time, i.e., the time that the zeolite and the phosphorus-containing source are maintained in contact with each other. With greater reaction times, all other factors being equal, a greater amount of phosphorus is incorporated with the zeolite. Other factors upon which the amount of phosphorus incorporated with the zeolite is dependent include reaction temperature, concentration of the treating compound in the reaction mixture, the degree to which the zeolite has been dried prior to reaction with the phosphorus-containing compound, the conditions of drying of the zeolite after reaction of the zeolite with the treating compound, and the amount and type of binder incorporated with the zeolite.

In practicing the desired alkylation process it may be desirable to incorporate the modified zeolite in another material resistant to the temperatures and other conditions employed in the alkylation process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Nauturally occurring clays which can be composited with the modified zeolite include those of the montmorillonite and kaolin families, which families include the subbentonites and the kaolins commonly known as Dixie, McNamee-Georgia and Florida clays or others in which the main mineral constituent is halloysite, Kaolinite, dickite, nacrite or anauxite. Such clays can be used in the raw state as originally mined or initially subjected to calcination, acid treatment or chemical modification.

In addition to the foregoing materials, the modified zeolites employed herein may be composited with a porous matrix material, such as silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of finely divided modified zeolite and inorganic oxide gel matrix may vary widely with the zeolite content ranging from between about 1 to about 99 percent by weight and more usually in the range of about 5 to about 80 percent by weight of the composite.

Exemplary of the hydrocarbons which may be alkylated by the process of this invention are aromatic compounds such as benzenes, naphthalines, anthracenes, and the like and substituted derivatives thereof; and alkyl substituted aromatics, e.g. toluene, xylene and homologs thereof.

In accordance with this invention the alkylating agents employed are olefinic hydrocarbons having from 2 to 20 carbon atoms such as ethylene, propylene, and dodecylene.

Operating conditions employed in the process of the present invention are critical and will be dependent, at least in part, on the specific alkylation reaction being effected. Such conditions as temperature, pressure, space velocity and molar ratio of the reactants and the presence of inert diluents will have important affects on the process. Accordingly, the manner in which these conditions affect not only the conversion and distribution of the resulting alkylated products but also the rate of deactivation of the catalyst will be described below.

The process of this invention is conducted such that alkylation of an aromatic hydrocarbon compound, exemplified by benzene, with an alkylating agent, i.e. an olefinic hydrocarbon exemplified by ethylene, is carried out in the vapor phase by contact in a reaction zone, such as, for example, a fixed bed of catalyst, under alkylation effective conditions, said catalyst being characterized as above-described and preferably hydrogen exchanged such that a predominate portion of its exchangeable cations are hydrogen ions. In general, it is contemplated that more than 50 percent and preferably more than 75 percent of the cationic sites of the crystalline aluminosilicate zeolite, above-described, will be occupied by hydrogen ions. The alkylatable aromatic compound and olefinic hydrocarbon are desirably fed to a first stage at an appropriate mole ratio of one to the other. The feed to such first stage is heated. After some reaction takes place, such as, for example, when about 80% of the olefinic hydrocarbon is consumed, the effluent of the first stage is cooled to remove heat of reaction and more olefinic hydrocarbon is added (second stage) to maintain the mole ratio of aromatic compound to olefinic hydrocarbon within the range established for the first stage. A plurality of reaction stages are possible for the process of this invention. It is generally desirable to provide cooling between reactor stages.

Considering vapor-phase alkylation of benzene with ethylene, the first stage mole ratio of benzene to ethylene may be in the range of about 1:1 to about 30:1. The first stage feed is heated to a reactor inlet temperature within the range of about 575°F. to about 900°F. at a pressure within the range of about atmospheric to about 300 psig. Preferred inlet temperatures fall within the range of about 600°F. to about 850°F. and preferred pressures fall within the range of about 25 psig to about 450 psig. The repeating of reaction staging is carried out while maintaining an overall aromatic hydrocarbon, e.g. benzene, to alkylating agent, e.g. ethylene, mole ratio of about 1:1 to about 30:1, with a preferred range of about 2.5:1 to about 25:1. As the reaction proceeds through the stages, the aromatic:alkylating agent mole ratio increases.

It is noted that extremely high total feed space velocities are possible in the process of this invention, i.e. up to 2000 lb. total feed/hr.-lb. crystalline alumino-silicate. An important factor in the present process is, however, the weight hourly space velocity (WHSV) of the alkylating agent, e.g. ethylene. The alkylating agent WHSV to each of any alkylation reactor stages is maintained between about 1 and about 10 lb. alkylating agent/hr.-lb. crystalline aluminosilicate. The most desirable ethylene, i.e. alkylating agent, WHSV is within the range of about 2 to about 8 lb. ethylene/hr.-lb. crystalline aluminosilicate. When the ethylene WHSV is maintained within the above limits, an economical cycle between regeneration of catalyst exists.

The process of this invention may be carried out as a batch-type, semi-continuous or continuous operation utilizing a fixed or moving bed catalyst system. A preferred embodiment entails use of a fluidized catalyst zone wherein the reactants, e.g. benzene and ethylene, are passed concurrently or countercurrently through a moving fluidized bed of the catalyst. The fluidized catalyst after use is conducted to a regeneration zone wherein coke is burned from the catalyst in an oxygen-containing atmosphere, e.g. air, at an elevated temperature, after which the regenerated catalyst is recycled to the conversion zone for furthur contact with the benzene and ethylene reactants.

Reactivation of the phosphorus modified zeolite catalyst can be effected by passing a vaporized phosphorus compound through the catalyst bed after the catalyst has been used for the desired alkylation. Thus, for example, after a period of continued use of the catalyst, it can be revivified by passage therethrough of a vaporized mixture, e.g. an equal volume mixture, of toluene and diphenyl phosphine chloride at an elevated temperature, i.e. about 250°C. over a ½ hour period of time. This treatment is then suitably followed by heating in air at 150 cc/minute at about 550°C. for approximately ½ hour.

The following examples will serve to illustrate the process of this invention without limiting the same:

EXAMPLE 1

Three grams of an HZSM-5 extrudate containing 65 weight percent HZSM-5 and 35 weight percent of alumina binder were refluxed with 45 ml. toluene for 1 hour. The mixture was then cooled and 1.15 grams of trimethylphosphate were added. Reflux was continued for an additional 16 hours and then the solvent was evaporated to yield the phosphorus modified catalyst. The theoretical weight percent phosphorus in the catalyst was 7.1 whereas the actual amount of phosphorus in the catalyst used was 4.7 weight percent.

A feed consisting of a mixture of benzene and ethylene in which the molar ratio of benzene to ethylene was 1.41 was passed over the above catalyst at a weight hourly space velocity of 7.51 and a temperature of 842°F.

A catalyst of 65 weight percent of HZSM-5 and 35 weight percent of alumina which had not undergone modification with phosphorous was likewise used under comparable experimental conditions.

The phosphorus-treated catalyst was found to produce a considerably purer ethylbenzene product with higher selectivity to ethylbenzene than the untreated catalyst as will be evident from the comparable data set forth in Table III.

TABLE III

| Catalyst | Unmodified Extrudate of HZSM-5 (65%) and Alumina (35%) | Catalyst of Example 1 — Phosphorus-Modified Extrudate of HZSM-5 (65%) and Alumina(35%) |
|---|---|---|
| Liquid Product Comp., Wt. % | | |
| Benzene | 57.94 | 50.25 |
| Toluene | 3.69 | 0.31 |
| Ethylbenzene | 26.38 | 38.45 |
| Para-xylene | 0.33 | Not detected |
| Meta-xylene | 0.57 | Not detected |
| Ortho-xylene/cumene | 1.30 | 0.44 |
| Styrene/n-propylbenzene | 1.84 | 0.75 |
| Para-ethyltoluene | 0.34 | 0.069 |
| Meta-ethyltoluene | 0.70 | 0.113 |
| Ortho-ethyltoluene/secondary butyl benzene | 0.37 | 0.047 |
| Para and Meta-diethylbenzene | 4.58 | 9.40 |
| Ortho-diethylbenzene | 0.34 | — |
| $C_{10}^{+}$ | 1.47 | 0.172 |

A further breakdown of impurities relative to ethylbenzene is shown in Table IV below.

TABLE IV

| Catalyst | Unmodified Extrudate of HZSM-5 (65%) and Alumina (35%) | Catalyst of Example 1 — Phosphorus-Modified Extrudate of HZSM-5 (65%) and Alumina (35%) |
|---|---|---|
| Impurities/Ethylbenzene, ppm | | |
| Ortho-xylene | 11,000 | ~1,350 |
| Cumene | 38,500 | 10,000 |
| n-propylbenzene | 70,000 | 19,500 |
| Toluene | 140,000 | 8,100 |
| | 259,500 | 38,950 |

It will be evident from the above data that the phosphorus-modified catalyst afforded an ethylbenzene product with considerably less impurities and in higher selectivity and yield.

EXAMPLE 2

Forty-five grams of an HZSM-5 extrudate containing 65 weight percent HZSM-5 and 35 weight percent of alumina binder were refluxed with 675 ml. toluene for 1 hour. The mixture was then cooled and 20.70 grams of trimethylphosphate were added. Reflux was continued for an additional 16 hours and then the solvent was evaporated to yield the phosphorous-modified catalyst having a theoretical phosphorous content of 8.26 weight percent. The catalyst was calcined at 500°C for 3 hours before testing. The actual amount of phosphorous on the catalyst after use was 4.7 weight percent.

A feed consisting of a mixture of benzene and ethylene in which the molar ratio of benzene to ethylene was 5.5 was passed over the catalyst at a weight hourly space velocity of 9.4 hour$^{-1}$ and a temperature of 752°F.

A catalyst of 65 weight percent of HZSM-5 and 35 weight percent of alumina which had not undergone modification with phosphorus was likewise used under comparable experimental conditions.

The phosphorus-treated catalyst was again found to produce a considerably purer ethylbenzene product than the untreated catalyst as will be evident from the comparable data set forth in Table V.

TABLE V

| Catalyst | Unmodified Extrudate of HZSM-5 (65%) and Alumina (35%) | Catalyst of Example 1 — Phosphorus-Modified Extrudate of HZSM-5 (65%) and Alumina (35%) |
|---|---|---|
| % P | 0 | 4.7 |
| Benzene/Ethylene (Mole) | 5.6 | 5.5 |
| WHSV | 9.6 | 9.4 |
| Temp., °F | 752 | 752 |
| Impurity/Ethylbenzene, ppm | | |
| Toluene | 10035 | 4170 |
| Para-xylene | 1845 | 450 |
| Meta-xylene | 3690 | 900 |
| Ortho-xylene | 1845 | 450 |
| Cumene | 2820 | 700 |
| n-Propylbenzene/Styrene | 6660 | 2000 |
| p-Ethyltoluene | 500 | 155 |
| m-Ethyltoluene/sec. Butylbenzene | 940 | 230 |
| $\geq C_{10}$ | 780 | small |
| | 30210 | 9530 |

EXAMPLE 3

Utilizing the catalyst of Example 1, a feed consisting of a mixture of benzene and ethylene in which the molar ratio of benzene to ethylene was 1.4 was passed over the catalyst at a weight hourly space velocity of 7.5 and a temperature of 570°F. The temperature was periodically raised to 750°F. and the catalyst performance was evaluated at this temperature.

A catalyst of 65 weight percent of HZSM-5 and 35 weight percent of alumina which had not undergone modification with phosphorus was likewise used under comparable experimental conditions. The effect of aging on ethylene conversion is shown in the attached single FIGURE of the drawing wherein ethylene conversion is plotted against hours on stream. Referring to this FIGURE it will be seen that the phosphorus-modified catalyst showed a slower aging rate than the unmodified catalyst. This unexpected result is highly advantageous since it affords means for increasing the cycle length between the catalyst regeneration thereby providing a definite economic advantage for the phosphorus-modified catalyst over the unmodified catalyst.

a pressure of zero psig and a weight hourly space velocity of 9.4 hour$^{-1}$.

The results obtained were compared with those obtained under identical conditions utilizing a catalyst of 65 weight percent of HZSM-5 and 35 weight percent of alumina which had not undergone modification with phosphorus. The results are set forth in TABLE VI.

TABLE VI

| Preparation Method | Unmodified Catalyst | Catalyst of Example 4 | Catalyst of Example 5 | Catalyst of Example 6 |
|---|---|---|---|---|
| % P (theoretical) | 0 | 7.11 | 8.6 | ~6.8 |
| Activity, $C_2H_4$ Conversion % | 97 | 98 | 93 | 96 |
| Product Purity Wt. Sel., Ethylbenzene + Diethylbenzene, % | 97.45 | 98.99 | 98.90 | 98.96 |
| Ortho-xylene + Cumene + Propylbenzene + Styrene/ Ethylbenzene, ppm | 11325 | 4035 | 4700 | 5620 |
| Impurities/Ethylbenzene, ppm | 28400 | 11200 | 12850 | 12100 |

EXAMPLE 4

Forty-five grams of an HZSM-5 extrudate containing 65 weight percent HZSM-5 and 35 weight percent of alumina binder were refluxed with 675 ml. toluene for 1 hour. The mixture was then cooled and 17.25 grams of trimethylphosphate were added. Reflux was continued for an additional 16 hours and then the solvent was evaporated to yield the phosphorus-modified catalyst having a theoretical phosphorus content of 7.11 weight percent. The catalyst was calcined 1 hour at 500°C and 13.5 hours at 450°C before testing. The actual amount of phosphorus on the catalyst after use was 4.9 weight percent.

EXAMPLE 5

Ten grams of an HZSM-5 extrudate containing 65 weight percent HZSM-5 and 35 weight percent of alumina binder were contacted with 14.0 grams of an aqueous solution of phosphoric acid containing 24.3 weight percent $H_3PO_4$. Impregnation of the catalyst was accomplished by subjecting the mixture to vacuum and releasing three times to fill the catalyst pores. The mixture was then evaporated to dryness under reduced pressure and calcined at 500°C. for 14 hours. The theoretical weight percent of phosphorus in the catalyst was 8.6. The actual amount of phosphorus on the catalyst after use was 7.3 weight percent.

EXAMPLE 6

Ten grams of HZSM-5 extrudate containing 65 weight percent HZSM-5 and 35 weight percent of alumina binder were soaked in an aqueous solution of phosphoric acid containing 30 grams of 85% $H_3PO_4$ diluted to 100 milliliters for 15 minutes. Excess solution was decanted and the catalyst was dried at 110°C. for 2 hours and calcined at 500°C. for about 14 hours before testing. The theoretical weight percent phosphorus in the catalyst was 6.8. The actual amount of phosphorus on the catalyst after use was 7.3 weight percent.

EXAMPLES 7–9

The catalysts of examples 4, 5, and 6 were used for alkylating benzene with ethylene employing a feed consisting of a mixture of benzene and ethylene in which the molar ratio of benzene to ethylene was 5.5. Reaction conditions included a temperature of 752°F.,

EXAMPLE 10

Ten grams of an HZSM-5 extrudate containing 65 weight percent HZSM-5 and 35 weight percent of alumina binder were contacted with a solution of 4.79 grams trimethylphosphate and 10.0 grams water. Impregnation of the catalyst was accomplished by subjecting the mixture to a vacuum and releasing three times to fill the catalyst pores. The mixture was then evaporated to dryness under reduced pressure and calcined at 500°C. for 14 hours. The theoretical weight percent of phosphorus in the catalyst was 8.5.

EXAMPLE 11

Ten grams of an HZSM-5 extrudate containing 65 weight percent HZSM-5 and 35 weight percent of alumina binder were contacted with a solution of 6.8 grams trimethylphosphate diluted to 20 cc. with water. After the mixture, was maintained for 15 minutes the liquid was decanted and the catalyst was dried at 110°C. for 1 hour and calcined at 500°C. for 14 hours. The actual amount of phosphorus on the catalyst after use was 3.1 weight percent.

EXAMPLE 12

A catalyst was prepared as described in Example 11 except that 5.8 grams methyl acid phosphate in 20 cc. of aqueous solution was substituted for aqueous trimethylphosphate. Methyl acid phosphate is a reaction product of methanol and phosphorus pentoxide which in this instance contained 26 weight percent phosphorous. The actual amount of phosphorus on the catalyst after use was 6.4 weight percent.

EXAMPLES 13–15

The catalysts of Examples 10–12 were used for alkylating benzene with ethylene employing a feed consisting of a mixture of benzene and ethylene in which the molar ratio of benzene to ethylene was 5.5. Reaction conditions included a temperature of 752°F., a pressure of zero psig and a weight hourly space velocity of 9.4. The reaction results were compared with those obtained under identical conditions utilizing a catalyst of 65 weight percent of HZSM-5 and 35 weight percent of alumina which had not undergone modification with phosphorus. The results are set forth in Table VII below.

TABLE VII

|  | Unmodified Catalyst | Catalyst of Example 10 | Catalyst of Example 11 | Catalyst of Example 12 |
| --- | --- | --- | --- | --- |
| % P | 0 | 8.5 | 3.1 | 6.4 |
| Activity |  |  |  |  |
| $C_2H_4$ Conversion, % | 97 | 97 | 98 | 96 |
| Product Purity |  |  |  |  |
| Wt. Sel., EB + DEB, % | 97.45 | 99.28 | 98.87 | 99.10 |
| O-xylene + Cumene + Propylbenzene + Styrene/Ethylbenzene, ppm | 11325 | 3634 | 6127 | 5926 |
| Impurities/Ethylbenzene, ppm | 28400 | 7786 | 12512 | 10590 |

EXAMPLE 16

Ten grams of an HZSM-5 extrudate containing 65 weight percent HZSM-5 and 35 weight percent alumina binder were contacted with water. The catalyst pores were filled by subjecting the mixture to vacuum and releasing three times. The excess water was decanted and the catalyst was calcined for ½ hour at 500°C. The entire impregnation-calcination procedure was repeated a total of five times.

The catalyst was used for alkylating benzene with ethylene employing a feed consisting of a mixture of benzene and ethylene in which the molar ratio of benzene to ethylene was 5.5. Reaction conditions included a temperature of 752°F., a pressure of zero psig and a weight hourly space velocity of 9.4 hour$^{-1}$.

The results obtained were compared with those obtained under identical conditions utilizing an untreated catalyst of 65 weight percent HZSM-5 and 35 weight percent of alumina. The results set forth in Table VIII below show that phosphorus is a necessary ingredient in the catalyst treatment.

TABLE VIII

|  | Unmodified Catalyst | Catalyst of Example 16 |
| --- | --- | --- |
| $C_2H_4$ Conversion, % | 97 | 100 |
| Wt. Sel., Ethylene + Diethylbenzene, % | 97.45 | 97.58 |
| Impurities/Ethylbenzene, ppm | 28400 | 26800 |

EXAMPLE 17

The catalyst of Example 4 was compared with an unmodified catalyst utilizing conditions of superatmospheric pressure. The conditions and results are set forth in Table IX below.

The results illustrate that a lower impurity level is exhibited by the phosphorus-modified catalyst under commercially attractive conditions.

TABLE IX

| Component | Unmodified Catalyst PPM Relative To Ethyl- benzene | Catalyst of Example 4 M Relative To Ethyl- benzene |
| --- | --- | --- |
| Toluene | 8300 | 3510 |
| P-xylene | 3060 | 840 |
| M-xylene | 6110 | 1690 |
| O-xylene/Cumene n-Propylbenzene/ | 5000 | 1950 |
| Styrene | 6110 | 2730 |
| p-Ethyltoluene | 110 | 130 |
| m-Ethyltoluene | 560 | 260 |
| o-Ethyltoluene/ sec-Butylbenzene | 1110 | 650 |
| $C_{10}$ | 940 | 0 |
|  | 31300 | 11760 |
| Time on Stream, Hr. | 6.5–72 | 30–95 |
| WHSV (Ethylene), Hr.$^{-1}$ | 4.26 | 4.05 |
| Benzene/Ethylene (Mole Ratio) | 8.04 | 8.72 |
| Temp., Inlet | 800°F. | 800°F. |
| Temp., Max. | 857°F. | 839°F. |
| Pressure, PSIG | 300 | 300 |

It will be evident from the foregoing examples that use of a phosphorus-modified crystalline alumino-silicate catalyst of the type defined hereinabove served to improve selectivity for the desired alkyl aromatic product, e.g. ethylbenzene with a substantial decrease in the formation of unwanted impurities. In addition, a phosphorus-modified catalyst markedly improved the aging characteristics of the catalyst during the alkylation reaction.

It is to be understood that the foregoing description is merely illustrative of preferred emdodiments of the invention of which many variations may be made by those skilled in the art within the scope of the following claims without departing from the spirit thereof.

I claim:

1. A process for effecting vapor phase alkylation of an aromatic hydrocarbon charge which comprises contacting said hydrocarbon charge with an olefinic hydrocarbon alkylating agent under conditions effective for accomplishing said vapor phase alkylation including a reactor inlet temperature between about 575°F. and about 900°F., a reactor pressure between atmospheric and about 3000 psig, employing a mole ratio of hydrocarbon charge to olefinic hydrocarbon alkylating agent in the approximate range of 1:1 to 30:1 and a weight hourly space velocity between about 2 and 2000 in the presence of a catalyst comprising a crystalline alumino-silicate zeolite, said zeolite having a silica to alumina ratio of at least about 12, a constraint index within the approximate range of 1 to 12, said catalyst having been modified by the addition thereto of phosphorus in an amount of at least about 0.5 percent by weight.

2. The process of claim 1 wherein said alkylating agent is an olefinic hydrocarbon containing from 2 to 20 carbon atoms.

3. The process of claim 1 wherein said crystalline aluminosilicate zeolite is characterized by a silica/alumina ratio in excess of 30.

4. The process of claim 1 wherein said crystalline zeolite is ZSM-5.

5. The process of claim 1 wherein phosphorus addition is accomplished as a result of contact of the crystalline aluminosilicate zeolite with a phosphorus compound.

6. The process of claim 5 wherein said phosphorus compound is trimethylphosphate.

7. The process of claim 5 wherein said phosphorus compound is phosphoric acid.

8. The process of claim 5 wherein said phosphorus compound is methyl acid phosphate.

9. The process of claim 5 wherein said phosphorus compound is a $P_2O_5^-$ alcohol reaction product.

10. The process of claim 1 wherein phosphorus is present in an amount of between about 0.5 and about 25 weight percent.

11. The process of claim 1 wherein said phosphorus is present in an amount of between about 2 and about 15 weight percent.

12. The process of claim 1 wherein the reactor inlet temperature is between about 600°F. and about 850°F. and the reactor pressure is between about 25 and about 450 psig.

13. The process of claim 1 wherein the crystalline aluminosilicate zeolite is combined in an amount between about 1 and about 90 weight percent in a binder therefor.

14. The process of claim 13 wherein said binder is alumina.

15. The process of claim 1 wherein said aromatic hydrocarbon is benzene and wherein said olefinic hydrocarbon alkylating agent is ethylene.

16. The process of claim 15 wherein the reactor temperature is between about 600°F. and about 850°F. and the reaction is between about 25 and about 450 psig.

17. The process of claim 15 wherein said phosphorus is present in an amount between about 0.7 and about 15 weight percent.

18. The process of claim 15 wherein said crystalline aluminosilicate zeolite is ZSM-5.

19. The process of claim 15 wherein the crystalline aluminosilicate zeolite is combined in an amount between about 1 and about 90 weight percent in a binder thereof.

20. The process of claim 19 wherein said binder is alumina.

* * * * *

UNITED STATES PATENT AND TRADEMARK OFFICE
CERTIFICATE OF CORRECTION

PATENT NO. : 3,962,364
DATED : June 8, 1976
INVENTOR(S) : LEWIS B. YOUNG

It is certified that error appears in the above—identified patent and that said Letters Patent are hereby corrected as shown below:

Title - Abstract Page [54] - "LUMINOSILICATE" should be --ALUMINOSILICATE--.

Column 1 - Title - "LUMINOSILICATE" should be --ALUMINOSILICATE--.

Column 14, line 50, Table V, "m-Ethyltoluene/" should be --m-Ethyltoluene--.

Column 14, line 50, Table V - Figures in Columns 2 and 3 under headings omitted. Insert --1095-- and --475-- respectively on line which reads "m-Ethyltoluene".

Column 14, line 51, Table V - After "m-Ethyltoluene" insert --o-Ethyltoluene/--.

Column 17, line 63, Table IX - Column 3 of Table, "M" should be --PPM--.

Column 18, line 20, Table IX - Column 3 of Table, "M" should be --PPM--.

Signed and Sealed this

Fourth Day of January 1977

[SEAL]

Attest:

RUTH C. MASON
*Attesting Officer*

C. MARSHALL DANN
*Commissioner of Patents and Trademarks*